(12) United States Patent
Roberts

(10) Patent No.: US 8,827,891 B2
(45) Date of Patent: Sep. 9, 2014

(54) SUSPENSION/RETRACTION DEVICE FOR SURGICAL MANIPULATION

(75) Inventor: Kurt Eric Roberts, New Haven, CT (US)

(73) Assignee: Yale University, New Haven, CT (US)

( * ) Notice: Subject to any disclaimer, the term of this patent is extended or adjusted under 35 U.S.C. 154(b) by 492 days.

(21) Appl. No.: 12/733,095

(22) PCT Filed: Aug. 8, 2008

(86) PCT No.: PCT/US2008/009530
§ 371 (c)(1),
(2), (4) Date: May 10, 2010

(87) PCT Pub. No.: WO2009/023136
PCT Pub. Date: Feb. 19, 2009

(65) Prior Publication Data
US 2010/0286473 A1    Nov. 11, 2010

Related U.S. Application Data

(60) Provisional application No. 60/964,319, filed on Aug. 10, 2007, provisional application No. 61/060,970, filed on Jun. 12, 2008.

(51) Int. Cl.
*A61B 1/32* (2006.01)
*A61M 5/178* (2006.01)
*A61M 31/00* (2006.01)

(52) U.S. Cl.
USPC ............... 600/37; 600/204; 600/210; 604/36; 604/164.09

(58) Field of Classification Search
USPC .................. 600/37, 201, 204, 207, 210, 235; 604/36, 164.1, 164.13, 510; 606/113
See application file for complete search history.

(56) References Cited

U.S. PATENT DOCUMENTS 5,242,456 A    9/1993  Nash et al.
5,415,666 A    5/1995  Gourlay et al.
(Continued)

FOREIGN PATENT DOCUMENTS

WO    WO2005/104927    11/2005
WO    WO2007/136683    11/2007
(Continued)

OTHER PUBLICATIONS

Single Port Laparoscopic Cholecystectomy With the Triport System: A Case Report, Romanelli et al., Surgical Innovation, vol. 15, No. 3, Sep. 2008, pp. 223-228.

(Continued)

*Primary Examiner* — John Lacyk
*Assistant Examiner* — Thaddeus Cox
(74) *Attorney, Agent, or Firm* — McCarter & English, LLP

(57) ABSTRACT

A device that can be delivered into a body cavity to manipulate tissue intracorporeally while being controlled extracorporeally and a method of using the device to perform a single-port laparoscopic or natural orifice surgery. The device is being capable of being passed through an interior diameter of a single port into the body cavity. The device comprises an anchor or suspension element that is attachable or mountable to the tissue intracorporeally, a guide element attached to the anchor or suspension element that allows for manipulation of at least one structure in at least one direction, and at least one structure attached to a suture or thread that is passable through the interior diameter of the port and positionable by the guide element. The structure is controllable extracorporeally by manipulating the suture or thread so that the structure moves in at least one direction intracorporeally.

24 Claims, 13 Drawing Sheets

(56) References Cited

U.S. PATENT DOCUMENTS

| | | |
|---|---|---|
| 6,358,196 B1 | 3/2002 | Rayman |
| 6,440,061 B1 * | 8/2002 | Wenner et al. .............. 600/114 |
| 7,270,672 B1 * | 9/2007 | Singer .......................... 606/148 |
| 7,691,103 B2 | 4/2010 | Fernandez et al. |
| 2002/0049367 A1 | 4/2002 | Irion et al. |
| 2004/0034345 A1 | 2/2004 | Lentz |
| 2004/0050395 A1 | 3/2004 | Ueda et al. |
| 2004/0111100 A1 | 6/2004 | Benderev et al. |
| 2005/0251207 A1 * | 11/2005 | Flores et al. ................. 606/232 |
| 2006/0149135 A1 * | 7/2006 | Paz ............................... 600/201 |
| 2006/0217681 A1 * | 9/2006 | Hart et al. .................... 604/506 |
| 2007/0156028 A1 * | 7/2007 | Van Lue et al. .............. 600/237 |
| 2008/0027476 A1 | 1/2008 | Piskun |
| 2009/0043246 A1 | 2/2009 | Dominguez |
| 2009/0131749 A1 | 5/2009 | Ahmed et al. |
| 2009/0326518 A1 | 12/2009 | Rabin |
| 2010/0081875 A1 | 4/2010 | Fowler et al. |
| 2010/0081880 A1 | 4/2010 | Widenhouse et al. |
| 2010/0094227 A1 | 4/2010 | Albrecht et al. |

FOREIGN PATENT DOCUMENTS

| | | |
|---|---|---|
| WO | WO 2008/045940 | 4/2008 |
| WO | WO2010/042913 | 4/2010 |

OTHER PUBLICATIONS

Emerging Technologies—Single-Incision Laparoscopic Surgery: How and Why?, Choi et al., Bariatric Times, Apr. 2009.

Role of Magnetic Anchors During Laparoendoscopic Single Site Surgery and NOTES, Raman et al., Journal of Endourology, vol. 23, No. 5, May 2009, pp. 781-786.

Retraction and triangulation with neodymium magnetic forceps for single-port laparoscopic cholecystectomy, Dominguez et al., Surg. Endosc, vol. 23, May 2009, pp. 1160-1666.

Single-incision laparoscopic surgery for cholecystectomy: an evolving technique, Chow et al., Surg. Endosc, vol. 24, Aug. 2009, pp. 709-714.

Single Port Approach to Surpass 20% of All Laparoscopic Procedures by 2014, PR Newswire, (No date).

European Search Report of European Application No. 08827410.5 dated Jul. 9, 2012.

* cited by examiner

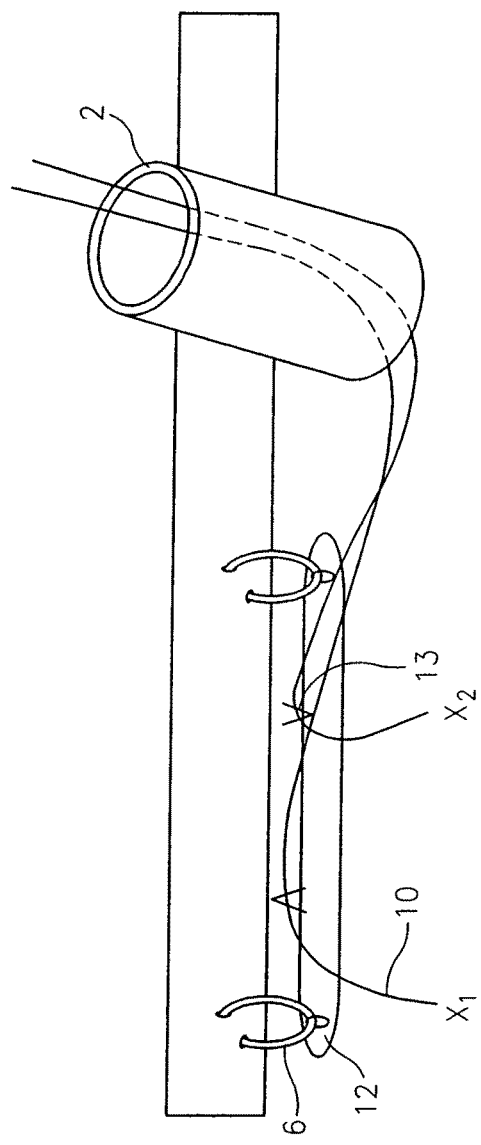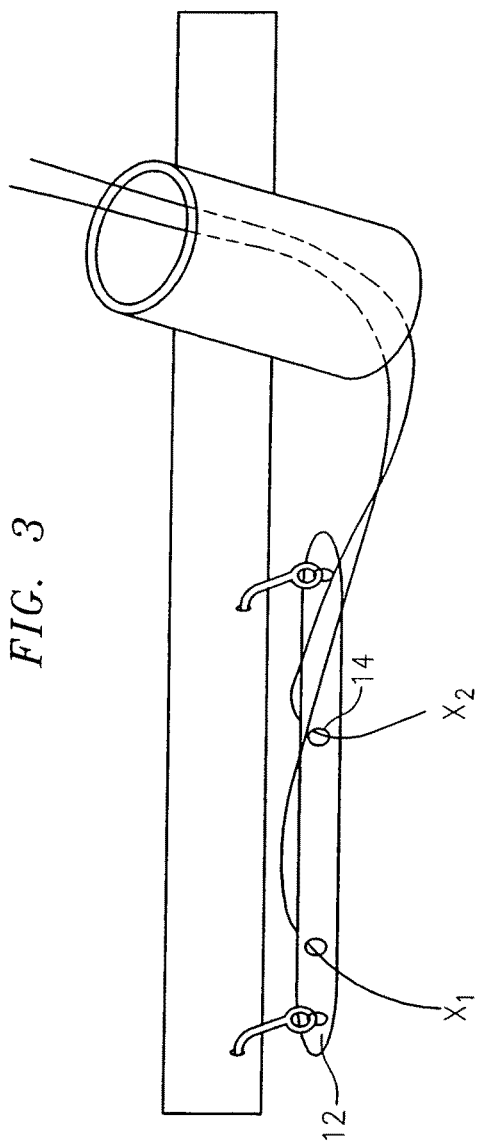

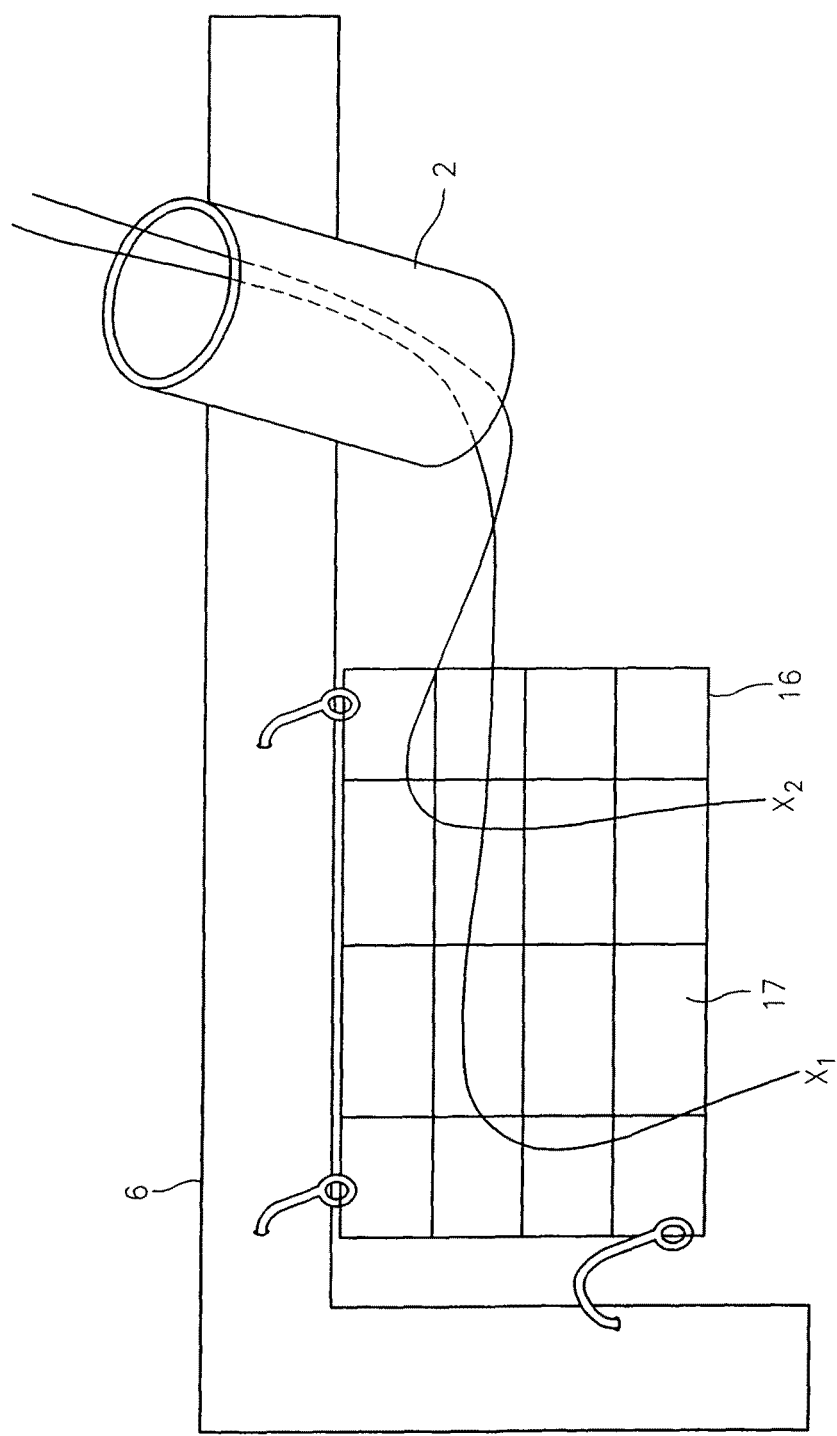

The attached string to appendix will be pulled thru loop and subsequently thru the port to allow for retraction of the appendix.

Appendix is pulled to abdominal wall to expose the base of the appendix for dissection.

Appendix is being placed in EndoCatch™ bag for retrieval.

SUSPENSION/RETRACTION DEVICE FOR SURGICAL MANIPULATION

CROSS REFERENCE TO RELATED APPLICATIONS

This application is a National Stage application of International Application No. PCT/US2008/009530, filed Aug. 8, 2008, which claims the benefit of U.S. Provisional Patent Application No. 60/964,319, filed on Aug. 10, 2007 and U.S. Provisional Patent Application No. 61/060,970, filed on Jun. 12, 2008, the subject mater of each of which is herein incorporated by reference in its entirety.

FIELD OF THE INVENTION

The present invention relates generally to an improved device for performing laparoscopic surgery and a method of using such a device to perform a single-port surgery.

BACKGROUND OF THE INVENTION

Laparoscopic surgery (which is also known as minimal invasive surgery (MIS)) has become increasingly popular over the last few years due to its benefits, including lower morbidity, less perceived pain, better cosmetic results and less hospital time. Laparoscopic surgery is one of the most commonly performed minimally invasive surgeries worldwide. Since its beginning, the advantages over an open surgical approach include, decreased pain, fewer postoperative complications, decreased length of hospitalization, better intra-abdominal visualization and better cosmetics are widely known and appreciated.

In laparoscopic surgery, small incisions, typically about 5 to about 15 millimeters in length, are made in the abdominal wall for the insertion of trocar ports (or other similar devices), which are thin tubes that span the thickness of the abdominal wall and allow for the insertion and extraction of the tools needed to perform the surgery.

In order to perform the surgery, the abdominal wall is pressurized with a gas (carbon dioxide) to a pressure of between about 10 and about 20 mm Hg to create a working space between the internal organs and the peritoneum. Typically the first tool introduced into and the last tool to be extracted from the abdominal cavity is an endoscope with its built in light source. The endoscope sends video images to a monitor that is used by the surgeon and medical staff to watch the introduction of other tools and, to make sure that such tools are properly introduced with no or minimal tissue damage.

In most laparoscopic surgeries, there are typically at least three tools that are required to perform the surgery—an endoscope, a grasper or lifter, and a cutting tool, which may be a scissor tool or electro-cautery. Furthermore, in a traditional laparoscopic surgical process, each tool that is needed/used requires its own trocar port. In addition, if access to a particular location is not possible from a current port, either a new port must be inserted or the tool in one of the other ports must be removed and then reinstalled.

There is always a risk of puncturing vital organs or blood vessels during the insertion of the trocar ports. Also, the repositioning of tools or the insertion of another port can result in a delay in the progress of the surgery, causing the patient to be under anesthesia for longer time periods and causing delays for the surgeon.

In the case of laparoscopic appendectomies, the classic laparoscopic technique typically utilizes three ports, which most commonly include one 12 mm and two 5 mm ports. The first port allows a laparoscope for visualization, the second harbors an instrument for dissection and the last port facilitates the use of an instrument for retraction of the appendix.

Over the past few years efforts have been made to reduce the number of ports required from three to two ports, or even a single port, and two-port techniques, hybrid approaches, and single-port assisted techniques have been developed in this regard. The two-port appendectomy technique is very similar to the standard three-port technique with the exception of one port allowing access for a rigid endoscope with a working channel and a second port that is used for a grasping instrument to provide retraction of the appendix.

In the hybrid technique, laparoscopy is combined with standard open techniques and the appendix is pulled out through the umbilicus in children or a right lower quadrant incision in adults to perform a traditional open appendectomy extracorporeally. The hybrid technique in which the appendix is pulled through a single incision in the umbilicus is only possible in the pediatric population because of the close proximity of the appendix and the umbilicus.

The single-port assisted technique uses one rigid endoscope with a working channel. The third port usually required for the retraction of the appendix is replaced by a sling suture that is put through the anterior abdominal wall in the right lower quadrant. The sling is then utilized to pull the appendix to the abdominal wall in order to provide the tension needed to perform the appendectomy intracorporeally. However, in order to place the transabdominal sling suture, the skin must be transversed twice with a needle to elevate the appendix to the abdominal wall.

Thus, it would be desirable to provide an improved laparoscopic technique that reduces the number of ports needed to perform laparoscopic surgery.

In addition, recent advances in laparoscopic surgical techniques have also allowed certain laparoscopic surgeries to be performed intraluminally, i.e., where access is gained through a natural orifice such as the vagina, rectum or esophagus. Thus, it would also be desirable to provide an improved technique for performing laparoscopic surgery intraluminally through a natural orifice.

SUMMARY OF THE INVENTION

It is an object of the present invention to provide an improved technique for laparoscopic surgery that promotes faster healing, less pain and less infection.

It is another object of the present invention to provide a single-port surgical technique as compared to the multiple-port techniques used previously.

It is still another object of the present invention to provide a puppeteer technique that allows a structure to be moved intracorporeally in various directions by controlling or manipulating the structure extracorporeally.

In one embodiment, the present invention relates generally to a device that can be delivered into a body cavity to manipulate tissue intracorporeally while being controlled extracorporeally, said device being capable of being passed through an interior diameter of a port into the body cavity, said device comprising:

a) an anchor or suspension means, wherein said anchor or suspension means is attached or mounted adjacent to tissue intracorporeally;

b) a guide means attached to the anchor or suspension means, where said guide means allows for manipulation of at least one structure in at least one direction; and c) at least one structure attached to a suture or thread that is passable through the interior diameter of the port and positionable by the guide means;

wherein the anchor or suspension means and the guide means provide leverage for moving the structure intracorporeally; and wherein the structure is controllable extracorporeally by manipulating the suture or thread, whereby the structure moves in at least one direction intracorporeally.

In another embodiment, the present invention relates to a kit for performing a single-port laparoscopic or natural orifice surgery comprising a device that can be delivered into a body cavity through a single port to manipulate tissue intracorporeally while being controlled extracorporeally, said device being capable of being passed through the single port into the body cavity, said kit comprising:

a) optionally, a trocar port;
b) an anchor or suspension element capable of passing through an inner diameter of the port, wherein said anchor or suspension element is attachable or mountable adjacent to an inner wall of the body cavity;
c) a guide element attached to the anchor or suspension element, where said guide element allows for manipulation of at least one structure in at least one direction; and
c) at least one structure attached to at least one suture that is passable through the inner diameter of the port and positionable in at least one direction by the guide element;

wherein the anchor or suspension element and the guide element provide leverage for moving the at least one structure intracorporeally within the body cavity; and wherein the at least one structure is controllable extracorporeally by manipulating the at least one suture, whereby the at least one structure moves in at least one direction intracorporeally within the body cavity.

In still another embodiment, the present invention relates generally to a method of performing a single-port laparoscopic or natural orifice surgery with a device comprising (i) an anchor or suspension element that is attachable or mountable to or mountable adjacent to an interior wall of the body cavity; (ii) at least one guide element attached to the anchor or suspension element, where said at least one guide element allows for manipulation of at least one structure in at least one direction; and (iii) at least one structure attached to at least one suture that is positionable in at least one direction by the guide element; wherein the device is capable of being delivered into a body cavity through a single port to manipulate tissue intracorporeally while being controlled extracorporeally, the method comprising the steps of:

a) making a single incision in the wall of the body cavity to create a single port through which the device is passed;
b) passing the anchor or suspension element through the interior diameter of the port and attaching the anchor or suspension element to or mounting the anchor or suspension element adjacent to the interior wall of the body cavity;
d) passing the at least one structure attached to the at least one suture through the at least one guide element; and
e) controlling the at least one structure intracorporeally by manipulating the at least one structure extracorporeally, whereby the at least one structure moves in at least one direction intracorporeally within the body cavity;

wherein the anchor or suspension element and the guide element provide leverage for moving the at least one structure intracorporeally within the body cavity.

BRIEF DESCRIPTION OF THE FIGURES

For a fuller understanding of the invention, reference is made to the following description taken in connection with the accompanying figures, in which:

FIG. 3 depicts a device that can be delivered into a body cavity in which the guide means comprises an elongated rigid member in accordance with another embodiment of the invention.

FIG. 4 depicts a variation of the elongated rigid member guide means depicted in FIG. 3.

FIG. 5 depicts a device that can be delivered into a body cavity in which the guide means comprises an openwork grid in accordance with another embodiment of the invention.

Also, while not all elements are labeled in each figure, all elements with the same reference number indicate similar or identical parts.

DETAILED DESCRIPTION OF THE PREFERRED EMBODIMENTS

Figure 1:
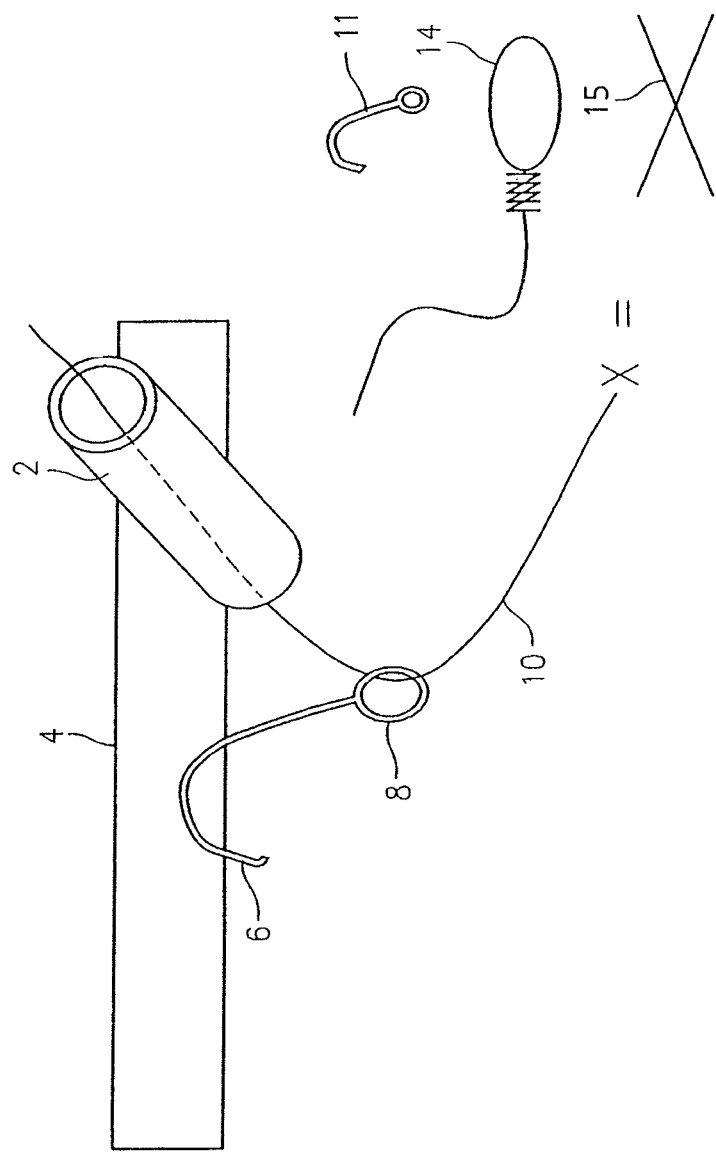
FIG. 1 depicts a device that can be delivered into a body cavity in which the guide means comprises a loop in accordance with a first embodiment of the invention.

The present invention relates generally to a device that can be delivered into a body cavity to manipulate tissue intracorporeally while being controlled extracorporeally. In one embodiment, the device may be wirelessly controlled extracorporeally. The device is designed to be capable of being passed through an interior diameter of an incision (port) into the body cavity.

The present invention relates generally to a laparoscopic technique that uses a single port without the need for any additional skin incisions or transdermally traversing needles and that is performed entirely intracorporeally. In addition, in one embodiment, the present invention allows the single incision to be placed anywhere on the abdominal wall to provide the ability to hide the resulting scar in the umbilicus or in the suprapubic hairline. It can be desirable for cosmetic reasons to move laparoscopic incisions to hide them in the suprapubic hairline by decreasing the length of the incisions visible on the anterior abdominal wall.

The single-port technique of the invention is usable to perform various laparoscopic procedures including laparoscopic exploration, laparoscopic cholecystectomy, laparoscopic common bile duct exploration, laparoscopic drainage of pancreatic pseudocysts, laparoscopic distal pancreatectomy, laparoscopic appendectomy, laparoscopic hernia repair, laparoscopic hiatal hernia repair, laparoscopic lumbar hernia repair, laparoscopic gastric bypass, laparoscopic splenectomy, laparoscopic Nissen fundoplication, laparoscopic Heller myotomy, laparoscopic left and right hemicolectomies, laparoscopic abdominal-perineal resection, laparoscopic Ripsten procedure, laparoscopic reversal of colostomy, laparoscopic adrenalectomy, laparoscopic nephrectomy, laparoscopic nephroureterectomy, laparoscopic pyeloplasty, laparoscopic prostatectomy, laparoscopic feeding jejunostomy, laparoscopic small bowel resection, laparoscopic gastro-entero anastomosis, laparoscopic gastrectomy, laparoscopic repair of duodenal ulcer, laparoscopic liver resection, laparoscopic hepatic artery balloon pump placement, laparoscopic tumor staging, laparoscopic anterior spinal fusion, laparoscopic exploration of chronic abdominal pain, laparoscopic placement of peritoneal dialysis catheter, laparoscopic esophagectomy, laparoscopic procedures for treatment of infertility related to polycystic ovarian syndrome, laparoscopic pelvic lymph node sampling, among others, given by way of example and not limitation.

The single-port technique of the invention generally employs an innovative "puppeteer technique" which utilizes a pulley or other means of providing leverage in the intra-abdominal cavity. In one embodiment, the pulley is in the form of an intraabdominally placed loop that is used as an axle to elevate the appendix to the abdominal wall with a string. In a manner similar to a puppeteer moving the limbs of his puppet(s) with a string, the surgeon pulls this string extracorporeally, which moves and retracts the appendix, by way of example and not limitation, to the abdominal wall. Thus, in most instances, no further incisions, ports, or transdermally traversing needles are needed. If necessary however, such as if complications arise, a second port may used to assist in the surgery.

In one embodiment, the device comprises:

a) an anchor or suspension means or element, wherein said anchor or suspension means or element is attached or mounted adjacent to tissue intracorporeally;

b) a guide means or element attached to the anchor or suspension means or element, where said guide means or element allows for manipulation of at least one structure in at least one direction; and c) at least one structure attached to a suture or thread that is passable through the interior diameter of the port and positionable by the guide means or element;

wherein the anchor or suspension means or element and the guide means or element provide leverage for moving the structure intracorporeally; and wherein the structure is controllable extracorporeally by manipulating the suture or thread, whereby the structure moves in at least one direction intracorporeally.

In one embodiment, the body cavity is an abdomen and said anchor or suspension means or element is intracorporeally attached to or mounted adjacent to an intraabdominal wall.

An example of a first embodiment of the device of the invention is depicted in FIG. 1 which shows a port 2 inserted into tissue 4. A hook 6 is used as the anchor or suspension means and is attached to a loop 8 which is used as the guide means. A structure X, which is attached to a suture 10 is then threaded through the loop 8 and is usable in the surgical procedure. In this example, X can be a hook 11, a noose 14 or a clamp or grasper 15.

The anchor or suspension means 6 can be any means that would be known to those skilled in the art for anchoring to tissue within the abdominal cavity. For example, the anchor or suspension means 6 may comprise at least one suture or at least one hook that is stitched or hooked into an intra-abdominal wall. In another embodiment, the anchor or suspension means 6 may comprises a plurality of magnets. In this embodiment, a corresponding plurality of magnets is provided extracorporeally to provide the magnetic force to hold the guide means or element, which is attached to the anchor or suspension means or element, in place intracorporeally.

The guide means can be any of a number of elements that are used to provide guidance and leverage to the at least one structure that is introduced through the port and into the body cavity. Examples of guide means that are usable in the practice of the invention include, for example, at least one of a loop 8, an elongated member 12 (depicted in FIG. 3) and an openwork grid 16 (depicted in FIG. 5). The guide means can be constructed of various materials, including for example, metals such as stainless steel and aluminum, various plastics, organic materials, natural and synthetic textiles, glass, and biodegradable materials, by way of example and not limitation.

In one embodiment, and as depicted in FIG. 1, the guide means or element is a loop 8 and the structure X with the suture 10 attached thereto is threaded through the loop 8. The loop 8 then acts as a fulcrum to create intra-abdominal tension and countertension to control the structure intracorporeally by manipulating the suture 10 extracorporeally, i.e., the structure X is a puppet that is manipulated by the string (suture). In another embodiment, the structure can be controlled intracorporeally by wireless means extracorporeally.

In another embodiment, as depicted in FIG. 3, the guide means or element is a semi-rigid elongated member 12 that has sufficient flexibility to bend without breaking. The elongated member 12 typically has one or more notches 13, one or more hooks, one or more loops 14 (depicted in FIG. 4), or other such "guiding" features mounted thereon or holes drilled therethrough so that the structure X can be threaded through the notches, hooks, loops or holes, to guide the structure X within the abdomen or body cavity and provide leverage to the structure as discussed above.

Figure 6A:
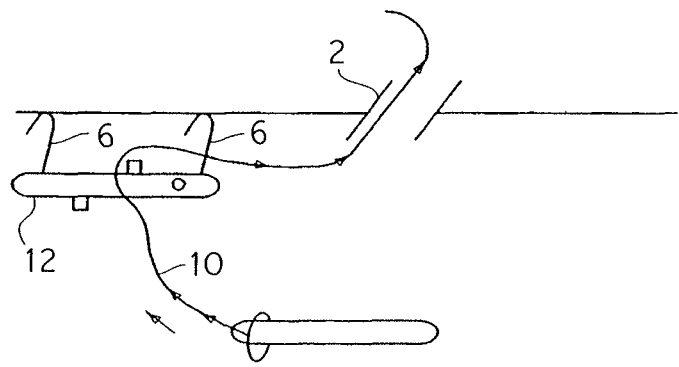
FIGS. 6A-6C depicts a variation of the elongated rigid member having telescoping portions.
Figure 6B:
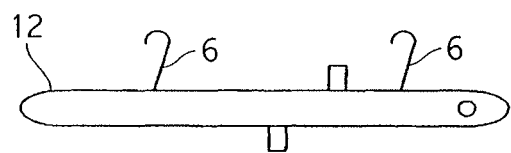
Figure 6C:
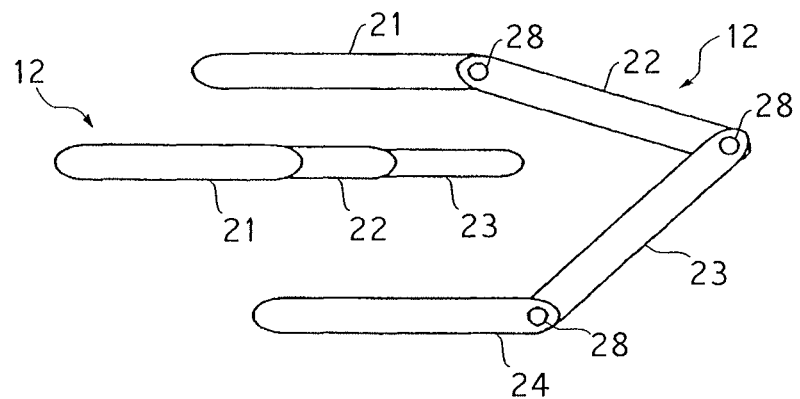

If desired, the elongated member 12 may comprise two or more rigid flexible portions as depicted in FIGS. 6A-6C. FIGS. 6A-6C depicts four portions 21, 22, 23 and 24 that are connected by means of joints or connectors 28. Thus the two or more portions 21, 22, 23, 24 can be folded onto one another to reduce the size of the elongated member 12 and facilitate easy entry and removal of the elongated member into and out of the body cavity. Furthermore, once the elongated member 12 is positioned within the body cavity and the first portion 21 is attached or mounted adjacent to the inner wall of the body cavity, the other portion(s) 22, 23 and 24 can be manipulated by the one or more sutures attached thereto to telescope the remaining portions into a desired position within the body cavity. In addition, these additional portions 22, 23, 24 can be sutured or otherwise attached to an inner wall of the body cavity to provide additional stability. Furthermore, while four portions are shown in FIGS. 6A-6C, the invention is not limited to four portions and may include as few as two and additional portions as needed to properly position the elongated member 12 within the body cavity.

In another embodiment of the invention, the guide means or element is an openwork grid 16 that is mounted substantially flush to a surface of the tissue with the anchor or suspension means. The openwork grid 16 comprises a plurality of openings 17 through which the at least one structure X is passed or guided. The openwork grid 16 can be introduced through the port by rolling the grid into the shape of a cylinder which is then unrolled once it is within the body cavity and is secured to the wall of the body cavity in several places. The openwork grid 16 can then be removed in a similar manner once surgery is completed, i.e., by rolling the grid 16 back into the shape of a cylinder.

The structure that is introduced into the abdomen can be any of a number of devices that are needed to perform various types of laparoscopic or other natural orifice or minimally invasive surgeries. For example, the structure can be selected from the group consisting of a noose, a bag, a receptacle, a hook, a grasper, a dissector, a manipulator, a clamp, a cutting implement, a scalpel, a scissors, a grabber, a lifter, a cauterizer, a dissector, an endoscope, a light or light delivery system, a sensor, an image sensor, a camera, including still and video cameras, a microrobot (such as described in U.S. Pat. No. 7,372,229 to Farritor et al., the subject mater of which is herein incorporated by reference in its entirety), and combinations of one or more of the foregoing. Other structures would also be known to those skilled in the art of particular laparoscopic, natural orifice and minimally invasive surgeries described herein and would be usable in the present invention.

Figure 2:
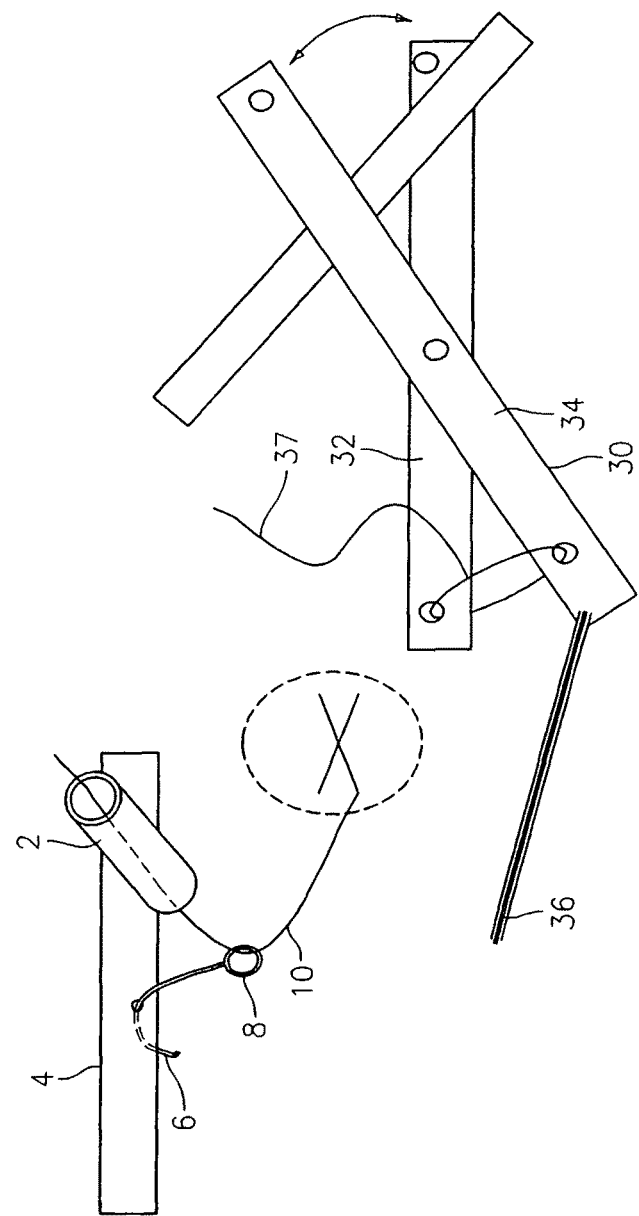
FIG. 2 depicts a device with a grasper or clamp in accordance another embodiment of the invention.

In one embodiment, as depicted in FIG. 2, the at least one structure is a grasper or clamp 30 having moveable pivotable blades or legs 32 and 34. This structure is then connected to one or more sutures 36 and 37 for manipulating the grasper or clamp 30. The structure may be tightened, released, or locked in place by manipulating the at least one suture 36 and 37 attached thereto. Thus the grasper or clamp structure 30 may be tightened, and/or released and/or locked in place to grasp or clamp body tissue or may be locked in place or tightened to facilitate removal of the grasper or clamp through the port.

In one embodiment, the structures may be pre-strung on the suture to facilitate ease of use.

The present invention also relates to a kit for performing a single-port laparoscopic or natural orifice surgery comprising a device that can be delivered into a body cavity through a single port to manipulate tissue intracorporeally while being controlled extracorporeally, said device being capable of being passed through the single port into the body cavity.

The kit typically comprises:
  a) optionally, a trocar port;
  b) an anchor or suspension means or element capable of passing through an inner diameter of the port, wherein said anchor or suspension means or element is attachable or mountable adjacent to an inner wall of the body cavity;
  c) a guide means or element attached to the anchor or suspension means or element, where said guide means or element allows for manipulation of at least one structure in at least one direction; and
  c) at least one structure attached to at least one suture that is passable through the inner diameter of the port and positionable in at least one direction by the guide means or element;
  wherein the anchor or suspension means or element and the guide means or element provide leverage for moving the at least one structure intracorporeally within the body cavity; and
  wherein the at least one structure is controllable extracorporeally by manipulating the at least one suture, whereby the at least one structure moves in at least one direction intracorporeally within the body cavity.

In a preferred embodiment, the body cavity is the abdominal cavity and the kit contains structures needed for a performing a specific laparoscopic surgical procedures such as those defined above.

In another embodiment, the kit is designed for performing a laparoscopic appendectomy and the at least one structure comprises at least one of a noose, a bag, a receptacle, a hook, a clamp, scissors, a dissector, an instrument to facilitate removal of at least a portion the appendix, and other structures which may be used in performing a laparoscopic appendectomy.

In a preferred embodiment, the port through which the at least one structure is passable has an interior diameter of between about 5 and about 25 mm.

In another embodiment, the present invention relates to a method of performing a single-port laparoscopic surgery with a device comprising (i) an anchor or suspension element that is attachable or mountable to or mountable adjacent to an interior wall of the body cavity; (ii) at least one guide element attached to the anchor or suspension element, where said at least one guide element allows for manipulation of at least one structure in at least one direction; and (iii) at least one structure attached to at least one suture that is positionable in at least one direction by the guide element; wherein the device is capable of being delivered into an abdominal body cavity through a single port to manipulate tissue intracorporeally while being controlled extracorporeally, the method comprising the steps of:
  a) making a single incision in the abdominal wall to create an opening in the abdominal wall through which the device is passed;
  b) passing the anchor or suspension element through the interior diameter of the port and attaching the anchor or suspension element to or mounting the anchor or suspension element adjacent to the intra-abdominal wall;
  c) passing the at least one structure attached to the at least one suture through the at least one guide element; and
  d) controlling the at least one structure intracorporeally by manipulating the at least one structure extracorporeally, whereby the at least one structure moves in at least one direction intracorporeally within the abdominal body cavity;
  wherein the anchor or suspension element and the guide element provide leverage for moving the at least one structure intracorporeally within the abdominal cavity.

In a preferred embodiment, prior to step c) the abdominal cavity is insufflated to a suitable pressure. The insufflation is typically performed using carbon dioxide or another suitable fluid or inert gas.

The present invention also relates to a method of performing a single-port laparoscopic or natural orifice surgery with a device comprising (i) an anchor or suspension element that is attachable or mountable to or mountable adjacent to an interior wall of the body cavity; (ii) at least one guide element attached to the anchor or suspension element, where said at least one guide element allows for manipulation of at least one structure in at least one direction; and (iii) at least one structure attached to at least one suture that is positionable in at least one direction by the guide element; wherein the device is capable of being delivered into a body cavity through a single port to manipulate tissue intracorporeally while being controlled extracorporeally.

The method generally comprises the steps of:
  a) making a single incision in the wall of the body cavity to create an opening through which the device is passed;

b) passing the anchor or suspension element through the interior diameter of the port and attaching the anchor or suspension element to or mounting the anchor or suspension element adjacent to the interior wall of the body cavity;

c) passing the at least one structure attached to the at least one suture through the at least one guide element; and d) controlling the at least one structure intracorporeally by manipulating the at least one structure extracorporeally, whereby the at least one structure moves in at least one direction intracorporeally within the body cavity.

As discussed above, the anchor or suspension element and the guide element provide leverage for moving the at least one structure intracorporeally within the body cavity.

The puppeteer technique of the invention has been found to provide adequate retraction to allow for dissection, ligation and transaction of the appendix at its base with no or minimal difficulties as discussed below in Example 1.

EXAMPLE 1

Single-Port Laparoscopic Appendectomy Performed on 14 Patients

During the study period, 17 patients with appendicitis presented to Yale New Haven Hospital (YNHH) when the inventor of the present invention as the surgeon on call for the Emergency General Surgery Service. Three patients were excluded according to established exclusion criteria. Thirteen of the remaining fourteen patients (8 females and 5 males) underwent a successful single-port laparoscopic appendectomy as described herein. No major complications were observed. One minor intraoperative complication was observed, in which the suprapubic access could be not be established safely and therefore an additional 5 mm port was placed infraumbilically. The laparoscopic appendectomy was then completed with 2 ports without further complications. One minor post-operative complication was seen in which a patient developed postoperative urinary retention, which resolved within 24 hours. Pathological examination revealed acute appendicitis in all but one case, in which signs of chronic inflammation of the appendix was identified. The individual patient characteristics are summarized in Table 1.

TABLE 1

Individual Patient Characteristics

| Patient | Gender | Age | BMI[1] | Access | OR-Time (min.) | Complications |
|---|---|---|---|---|---|---|
| 1 | F | 22 | 25.3 | TU[2] | 115 | |
| 2 | M | 46 | 28.3 | TU | 123 | |
| 3 | M | 29 | 29.8 | TU | 92 | |
| 4 | M | 40 | 19.4 | TU | 67 | |
| 5 | F | 47 | 31.1 | TU | 84 | |
| 6 | F | 37 | 36.0 | TU | 63 | |
| 7 | F | 35 | 39.0 | TU | 74 | |
| 8 | F | 40 | 20.4 | SP[3] | 54 | |
| 9 | F | 29 | 32.4 | SP | 95 | Urinary retention |
| 10 | F | 33 | 29.0 | SP | 128 | |
| 11 | F | 22 | 23.4 | SP | 87 | |
| 12 | M | 25 | 20.5 | SP | 68 | Inability to gain access-converted to two-port appendectomy |
| 13 | M | 59 | 27.5 | TU | 77 | |

TABLE 1-continued

Individual Patient Characteristics

| Patient | Gender | Age | BMI[1] | Access | OR-Time (min.) | Complications |
|---|---|---|---|---|---|---|
| 14 | M | 49 | 22.0 | TU | 79 | |
| | 61% F | 37.5 | | | | |

[1]Body mass index
[2]Transumbilical
[3]suprapubic

The patients were positioned in a steep Trendelenberg position and left side down to aid in the visualization of the inflamed appendix. One 11 mm trocar is then placed infraumbilically or alternatively in the suprapubic hairline, via the Versastep® Veress system (available from Covidien AG, North Haven, Conn.). After access was successfully gained, a 10 mm rigid endoscope with a 5 mm working channel (available from Karl Storz, Tuttlingen, Germany) was used for the majority of the surgery. Intermittently, a 5 mm, 30° angled endoscope was needed to allow for the use of a 5 mm Ligasure® device (available from Covidien AG, North Haven, Conn.) for dissection and coagulation of the mesoappendix. This step is important because the working channel of the endoscope is typically too narrow to allow for the use of the Ligasure® device through the working channel. However, if an endoscope with a large enough working channel was used, this step would likely not be needed.

Figure 7:
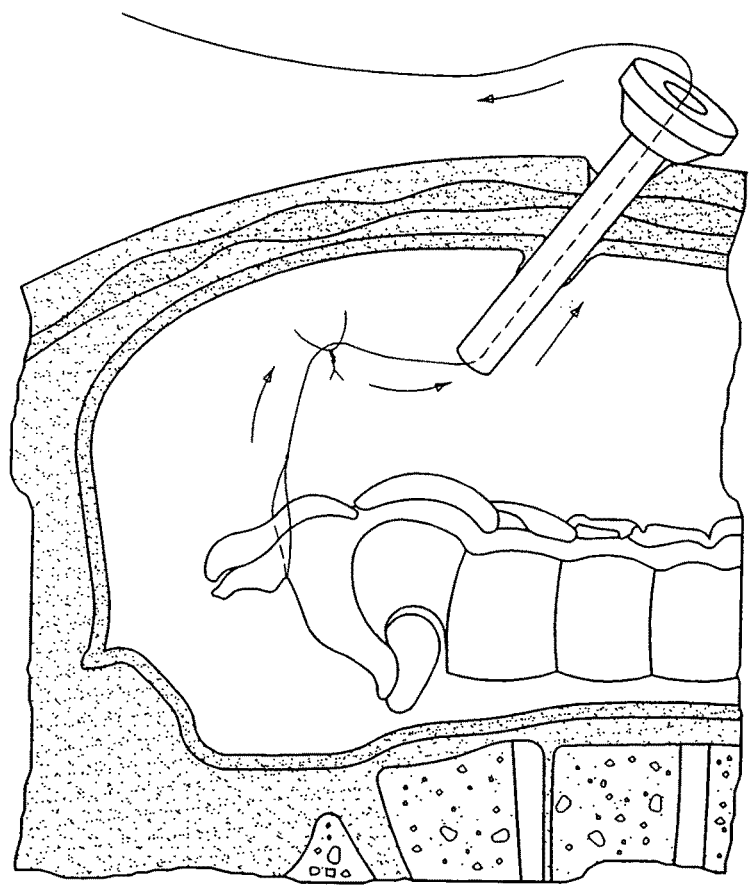
FIG. 7 depicts a basic principle of the novel technique of the invention as applied to a laparoscopic appendectomy.

Retraction for the ability to dissect between the appendiceal artery and the base of the appendix was achieved by pulling the appendix lateral, anterior and cephalad in the manner indicated in FIG. 7.

Figure 8:
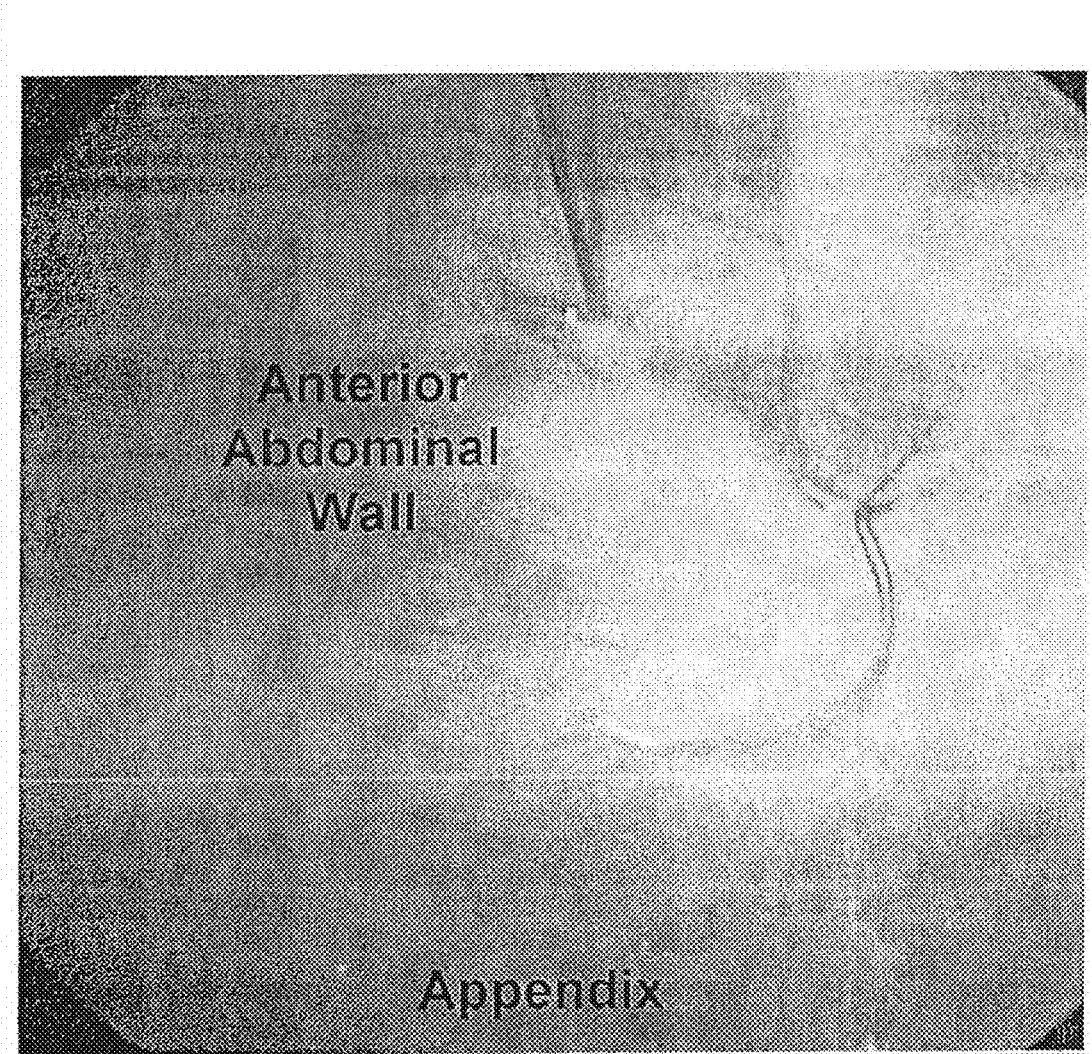
FIG. 8 depicts a laparoscopic appendectomy performed in accordance with the present invention in which a 0-polysorb stitch is being placed to the anterior abdominal wall for the creation of the loop to be used as the guide means of the invention.

First, in order to achieve the fulcrum effect, a "pulley" was created by mounting a loop tied as an air knot (0-Polysorb®, available from Covidien AG, North Haven, Conn.) to the anterior abdominal wall within the abdominal cavity just cephalad and lateral to the base of the appendix. The loop is subsequently used as an axle as illustrated in FIG. 8.

Figure 9:
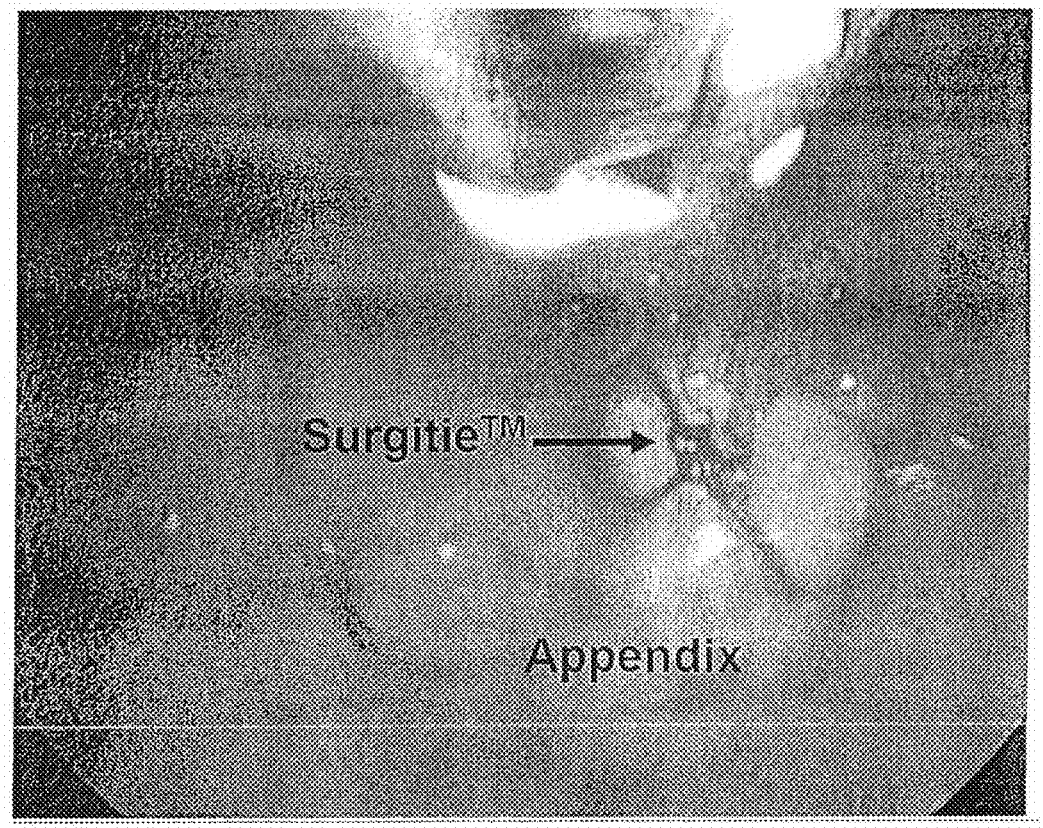
FIG. 9 depicts a laparoscopic appendectomy performed in accordance with the present invention in which the appendix is getting caught by Surgitie® for later retraction.
Figure 10:
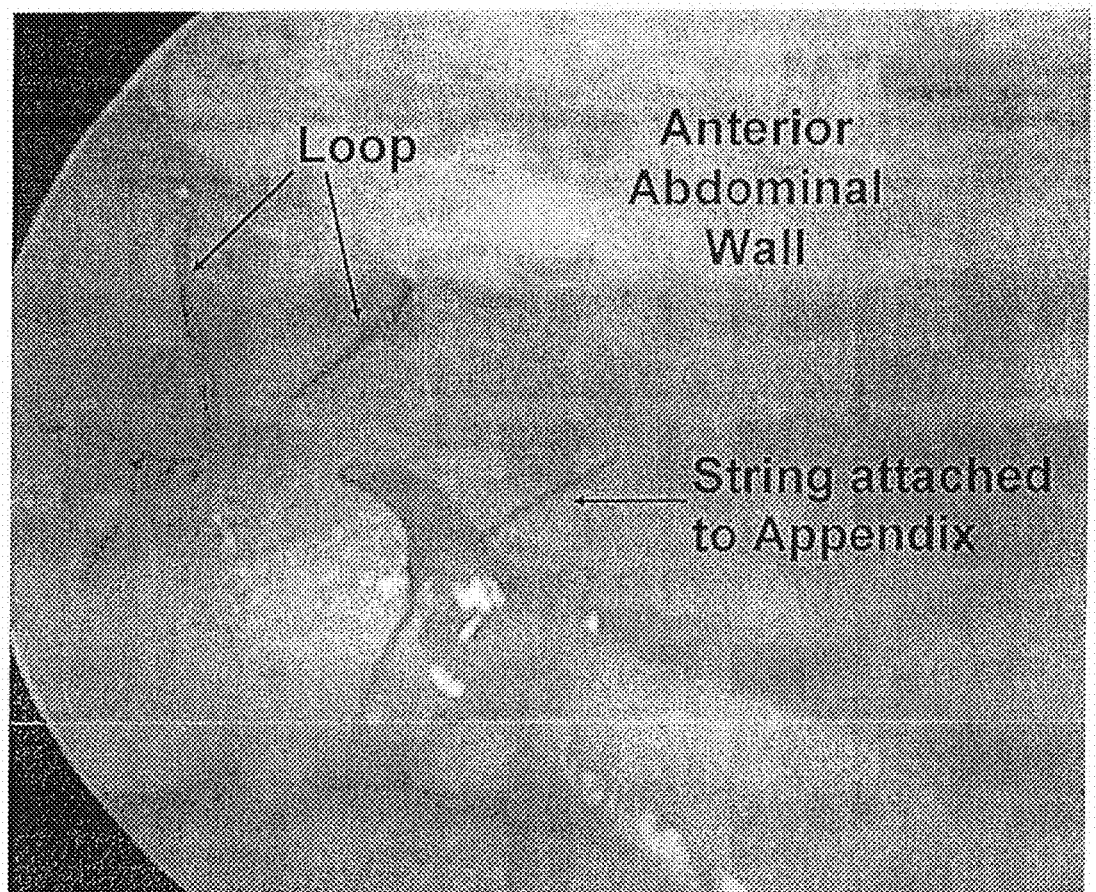
FIG. 10 depicts a laparoscopic appendectomy performed in accordance with the present invention in which the attached string/suture to the appendix is pulled through the loop and subsequently through the port to allow for retraction of the appendix.
Figure 11:
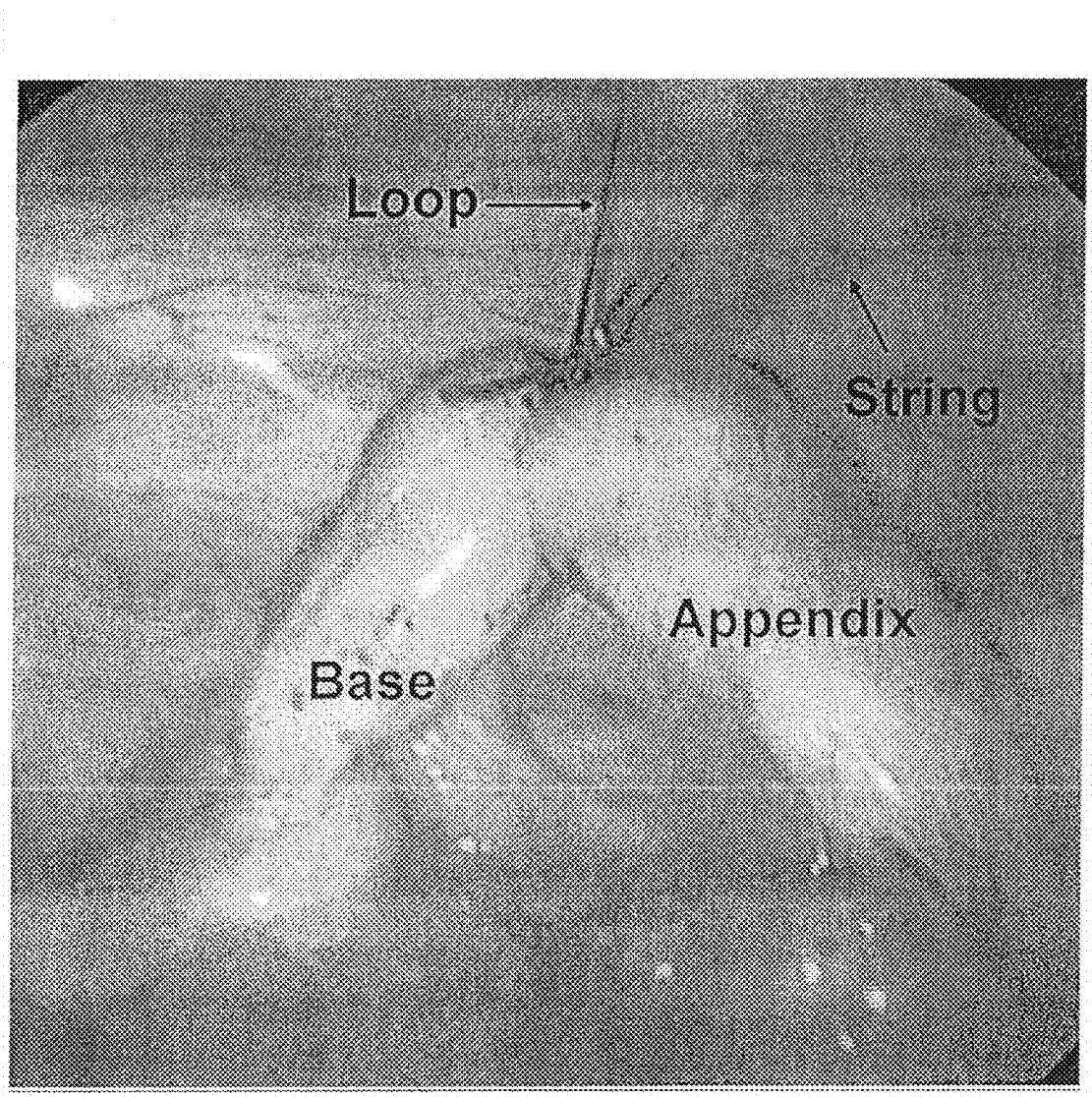
FIG. 11 depicts a laparoscopic appendectomy performed in accordance with the present invention in which the appendix is pulled to the abdominal wall to expose the base of the appendix for dissection.
Figure 12:
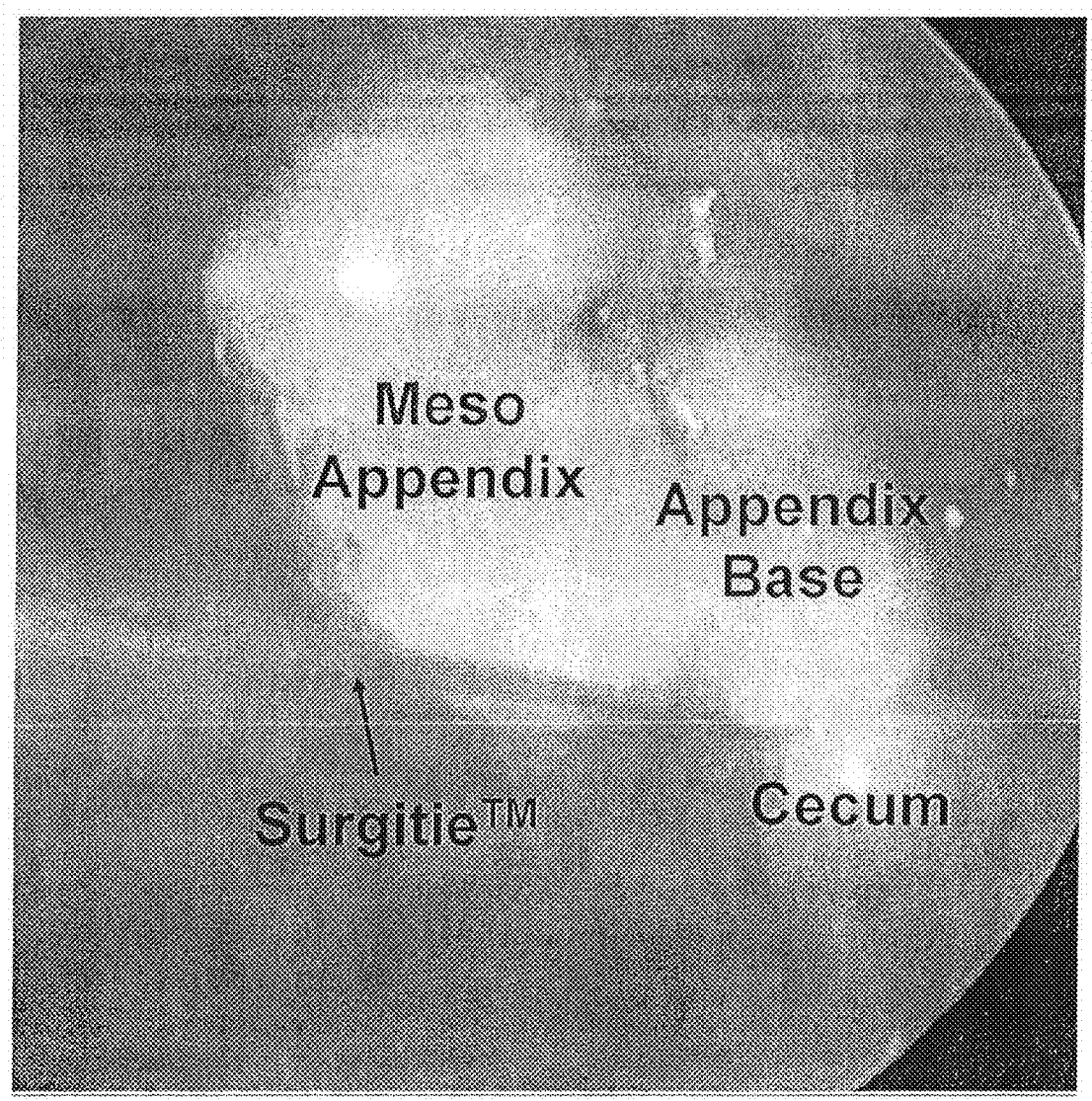
FIG. 12 depicts a laparoscopic appendectomy performed in accordance with the present invention in which ligation at the base of the appendix with Surgitie® is shown.

Next, a string (Surgitie®, available from Covidien AG, North Haven, Conn.) was placed around the appendix, as illustrated in FIG. 9. The string was threaded though the previously created loop and pulled through the 11 mm port to rest extracorporeally as illustrated in FIG. 10. This enabled the surgeon to pull on the string extracorporeally like a "puppeteer", which resulted in a lateral and anterior movement of the appendix to the abdominal wall, exposing the base of the appendix, as illustrated in FIG. 11. Then, the mesoappendix was dissected from the appendiceal base using a Maryland dissector. The Ligasure® device was used to seal and divide the mesoappendix, or a tie (0-Polysorb®) is used for ligation of the mesoappendix as depicted in FIG. 12.

Figure 13:
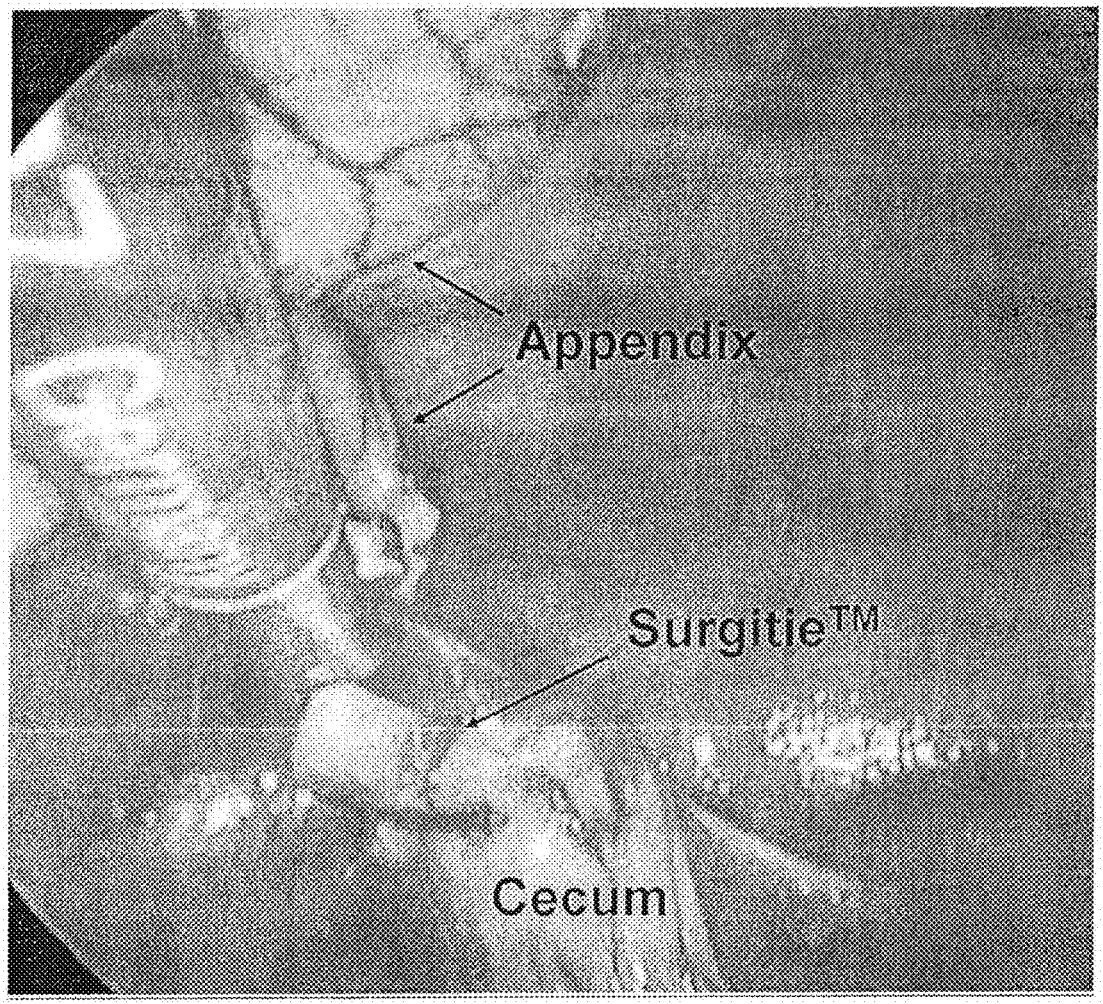
FIG. 13 depicts a laparoscopic appendectomy performed in accordance with the present invention in which the appendix is being transected.
Figure 14:
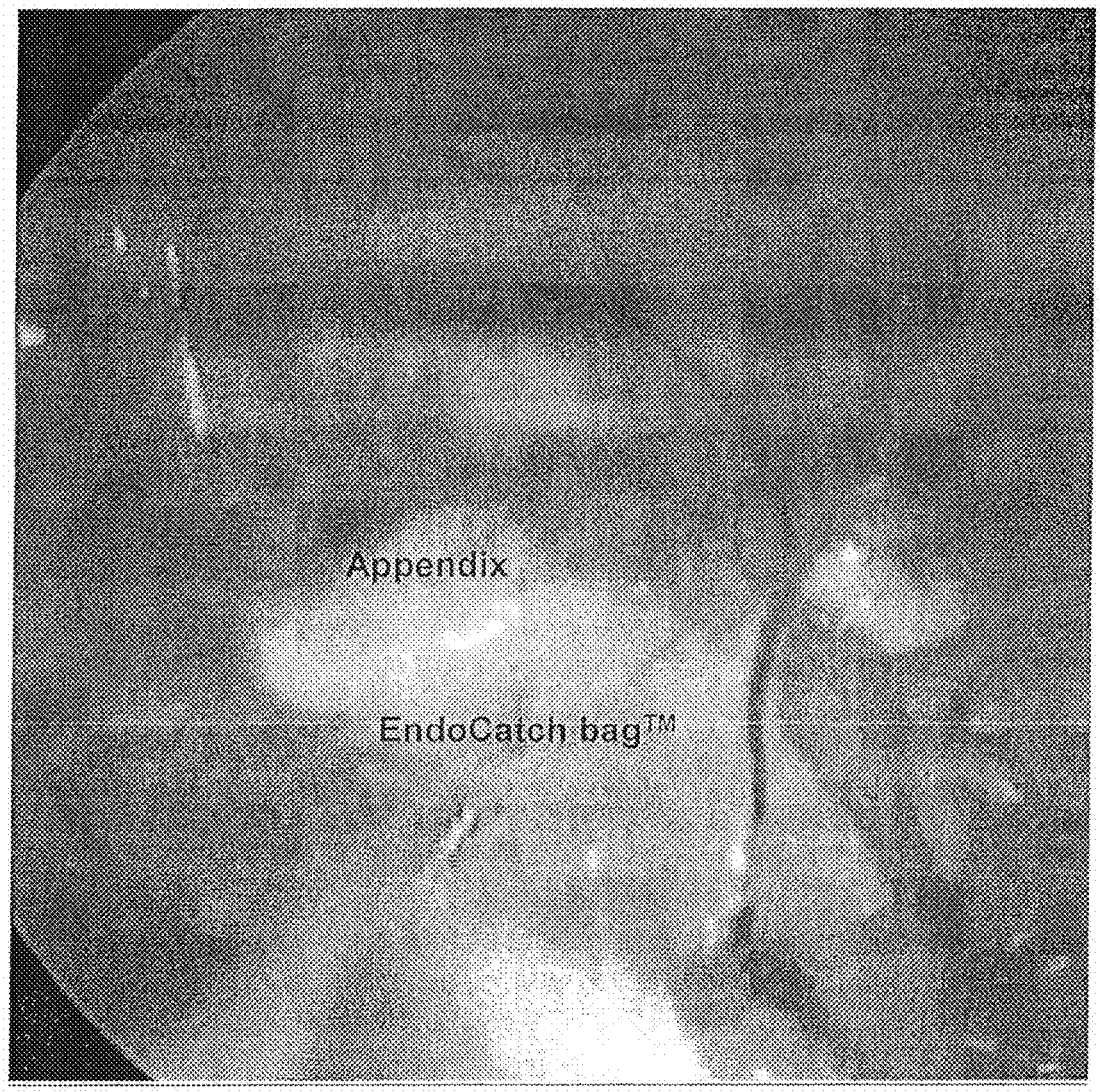
FIG. 14 depicts a laparoscopic appendectomy performed in accordance with the present invention in which the appendix is being placed in an EndoCatch® bag for retrieval.

Subsequently, another tie (0-Polysorb, available from Covidien AG, North Haven, Conn.) was placed around the appendix and divided using scissors, as illustrated in FIG. 13. The appendix was then placed in an EndoCatch® bag (available from Covidien AG, North Haven, Conn.) and retrieved from the patient's abdomen, as depicted in FIG. 14. The loop or "pulley" was then cut and removed. The 11 mm fascial defect was then closed with a 0-Polysorb statute in a FIG. 8 configuration. In the final step of the procedure, the skin was approximated with a simple interrupted 4-0 Caprosyn and Indermil® (available from Covidien AG, North Haven, Conn.) was applied.

As discussed above, the laparoscopic incision can be placed either transumbilically or in the suprapubic hairline. Applicant notes that the suprapubic approach has been associated with several complications due to following reasons. Firstly, there may be an inability to access the abdominal cavity safely, because of an incorrect insufflation and dissection with carbon dioxide of the preperitoneal space at the beginning of the operation which widened the space between the fascia and the peritoneum, and made a safe access difficult. Therefore, it may be necessary to use a primary transumbilical access. Secondly, another possible result of carbon dioxide dissection of the perperitoneal space my lead to post-operative urinary retention due to irritation of the bladder. Thus it is seen that both complications seem to be caused by preperitoneal insufflation with carbon dioxide. To avoid this problem, it may be preferred to use an open Hassan technique or another access method that provides visualization of the intraperitoneal space prior to insufflation with carbon dioxide which would prevent insufflation of the preperitoneal space with carbon dioxide.

While the example is shown as it relates to a laparoscopic appendectomy technique, the invention is not limited to appendectomies but is generally applicable to other laparoscopic and natural orifice surgery techniques that have previously required multiple ports to perform.

Finally, while the invention has been particularly shown and described with respect to preferred embodiments thereof, it will be understood that changes in form and details may be made therein without departing from the scope and spirit of the invention.

What is claimed is:

1. A system for performing a single-port laparoscopic or natural orifice surgery that can be at least partially delivered into a body cavity to manipulate tissue intracorporeally while being controlled extracorporeally, the system being capable of being passed through an interior diameter of a port into the body cavity, the system comprising:
   a) an anchor or suspension means, wherein the anchor or suspension means is attached or mounted adjacent to the tissue intracorporeally;
   b) a guide means attached to the anchor or suspension means, wherein the guide means allows for dynamic manipulation of at least one structure in at least one direction; and
   c) the at least one structure attached to a suture that is passable through the interior diameter of the port and positionable by the guide means;
   wherein the anchor or suspension means and the guide means provide leverage for moving the at least one structure intracorporeally;
   wherein the guide means defines at least one of a loop, a notch, a grid or a hook through which the suture passes;
   wherein the suture defines three segments including (i) a first segment extending from an extracorporeal position of the port, through the interior diameter of the port and to an intracorporeal position of the port inside the body cavity, (ii) a second segment extending from the intracorporeal position of the port to the anchor or suspension means, and (iii) a third segment extending from the anchor or suspension means to the tissue,
   wherein the second segment defines a lateral spacing between the intracorporeal position of the port and the anchor or suspension means; and
   wherein the at least one structure is controllable relative to the tissue extracorporeally by dynamically manipulating the suture extending from the interior diameter of the port extracorporeally, whereby the at least one structure moves in the at least one direction intracorporeally.

2. The system according to claim 1, wherein the body cavity is an abdominal cavity and the anchor or suspension means is intracorporeally attached to or mounted adjacent to an intra-abdominal wall.

3. The system according to claim 1, wherein the anchor or suspension means comprises the suture, at least one hook, a plurality of magnets, or combinations of one or more of the foregoing.

4. The system according to claim 3, wherein the anchor or suspension means comprises the plurality of magnets and a corresponding plurality of magnets is provided extracorporeally to provide a magnetic force to hold the guide means in place intracorporeally.

5. The system according to claim 1, wherein the guide means is an elongated member and comprises at least one of the loop, the notch, or the hook mounted thereon through which the at least one structure is passed or guided.

6. The system according to claim 5, wherein the elongated member comprises two or more portions that are connected by means of joints or connectors,
   wherein the two or more portions are folded onto one another to facilitate easy entry and removal of the elongated member into the body cavity; and
   wherein once the elongated member is positioned within the body cavity and a first portion is attached or mounted adjacent to an inner wall of the body cavity, at least a second portion is manipulated by the suture or thread to telescope the at least second portion into a desired position in the body cavity.

7. The system according to claim 6, wherein the at least second portion of the elongated member is attached to the inner wall of the body cavity.

8. The system according to claim 1, wherein the grid is mounted substantially flush to a surface of the tissue with the anchor or suspension means, the grid comprising a plurality of openings through which the at least one structure is passed or guided.

9. The system according to claim 1, wherein the at least one structure is selected from the group consisting of a noose, a bag, a receptacle, a hook structure, a grasper, a dissector, a manipulator, a clamp, a cutting implement, a scalpel, a scissors, a grabber, a lifter, a cauterizer, a dissector, an endoscope, a light or light delivery system, a sensor, an image sensor, a camera, including still and video cameras, a microrobot and combinations of one or more of the foregoing.

10. The system according to claim 9, wherein the at least one structure is the grasper or the clamp having moveable pivotable blades or legs, the at least one structure being connected to the suture for manipulating the grasper or the clamp,
   wherein the grasper or the clamp is tightened, released, or locked in place by manipulating the suture attached thereto;
   wherein the grasper or the clamp is at least one of tightened, released, and locked in place to grasp or clamp the tissue; and
   wherein the grasper or the clamp is at least one of locked in place and tightened to facilitate removal of the grasper or the clamp through the port.

11. The system according to claim 10, wherein the at least one structure is pre-strung on the suture.

12. A kit for performing a single-port laparoscopic or natural orifice surgery comprising a system that can be at least partially delivered into a body cavity through a single port to manipulate tissue intracorporeally while being controlled extracorporeally, the system being capable of being passed through the single port into the body cavity, the kit comprising:

a) optionally, a trocar port;
b) an anchor or suspension means capable of passing through an inner diameter of the single port, wherein the anchor or suspension means is attachable or mountable adjacent to an inner wall of the body cavity;
c) a guide means attached to the anchor or suspension means, wherein the guide means allows for dynamic manipulation of at least one structure in at least one direction; and
d) the at least one structure attached to a suture that is passable through the inner diameter of the single port and positionable in the at least one direction by the guide means;
wherein the anchor or suspension means and the guide means provide leverage for moving the at least one structure intracorporeally within the body cavity;
wherein the guide means defines at least one of a loop, a notch, a grid or a hook through which the suture passes;
wherein the suture defines three segments including (i) a first segment extending from an extracorporeal position of the single port, through the interior diameter of the single port and to an intracorporeal position of the single port inside the body cavity, (ii) a second segment extending from the intracorporeal position of the single port to the anchor or suspension means, and (iii) a third segment extending from the anchor or suspension means to the tissue,
wherein the second segment defines a lateral spacing between the intracorporeal position of the single port and the anchor or suspension means; and
wherein the at least one structure is controllable relative to the tissue extracorporeally by dynamically manipulating the suture extending from the interior diameter of the single port extracorporeally, whereby the at least one structure moves in the at least one direction intracorporeally within the body cavity.

13. The kit according to claim 12, wherein the body cavity is an abdominal cavity.

14. The kit according to claim 12, wherein the kit is for performing a laparoscopic appendectomy and the at least one structure comprises at least one of a noose, a bag, a receptacle, a hook structure, a clamp, scissors, a dissector and an instrument to facilitate removal of at least a portion an appendix.

15. The kit according to claim 12, wherein the single port through which the at least one structure is passable includes an interior diameter of between about 5 mm and about 25 mm.

16. A kit for performing a single-port laparoscopic or natural orifice surgery comprising a system that can be at least partially delivered into a body cavity through a single port to manipulate tissue intracorporeally while being controlled extracorporeally, the system being capable of being passed through the single port into the body cavity, the kit comprising:
a) optionally, a trocar port;
b) an anchor or suspension element capable of passing through an inner diameter of the single port, wherein the anchor or suspension element is attachable or mountable adjacent to an inner wall of the body cavity;
c) a guide element attached to the anchor or suspension element, wherein the guide element allows for dynamic manipulation of at least one structure in at least one direction; and
d) the at least one structure attached to a suture that is passable through the inner diameter of the single port and positionable in the at least one direction by the guide element;
wherein the anchor or suspension element and the guide element provide leverage for moving the at least one structure intracorporeally within the body cavity;
wherein the guide element defines at least one of a loop, a notch, a grid or a hook through which the suture passes;
wherein the suture defines three segments including (i) a first segment extending from an extracorporeal position of the single port, through the interior diameter of the single port and to an intracorporeal position of the single port inside the body cavity, (ii) a second segment extending from the intracorporeal position of the single port to the anchor or suspension element, and (iii) a third segment extending from the anchor or suspension element to the tissue,
wherein the second segment defines a lateral spacing between the intracorporeal position of the single port and the anchor or suspension element; and
wherein the at least one structure is controllable relative to the tissue extracorporeally by dynamically manipulating the suture extending from the interior diameter of the single port extracorporeally, whereby the at least one structure moves in the at least one direction intracorporeally within the body cavity.

17. A method of performing a single-port laparoscopic surgery with a system comprising (i) an anchor or suspension means that is attachable or mountable to or mountable adjacent to an interior wall of a body cavity; (ii) at least one guide means attached to the anchor or suspension means, wherein the at least one guide means allows for dynamic manipulation of at least one structure in at least one direction; and (iii) the at least one structure attached to a suture that is positionable in the at least one direction by the at least one guide means; wherein the system is capable of being at least partially delivered into the body cavity through a single port to manipulate tissue intracorporeally while being controlled extracorporeally, the method comprising:
a) making a single incision in an abdominal wall to create an opening in the abdominal wall through which the system is passed;
b) passing the anchor or suspension means through an interior diameter of the single port and attaching the anchor or suspension means to or mounting the anchor or suspension means adjacent to an intra-abdominal wall;
c) passing the at least one structure attached to the at least one suture through the at least one guide means attached to the anchor or suspension means; and
d) controlling the at least one structure intracorporeally by dynamically manipulating the suture extracorporeally, whereby the at least one structure moves in the at least one direction intracorporeally within the body cavity;
wherein the at least one guide means defines at least one of a loop, a notch, a grid or a hook through which the suture passes;
wherein the suture defines three segments including (i) a first segment extending from an extracorporeal position of the single port, through the interior diameter of the single port and to an intracorporeal position of the single port inside the body cavity, (ii) a second segment extending from the intracorporeal position of the single port to the anchor or suspension means, and (iii) a third segment extending from the anchor or suspension means to the tissue,
wherein the second segment defines a lateral spacing between the intracorporeal position of the single port and the anchor or suspension means; and wherein the anchor or suspension means and the guide means provide leverage for moving the at least one structure intracorporeally within the body cavity.

18. The method according to claim 17, comprising insufflating the body cavity to a suitable pressure prior to step b).

19. A method of performing a single-port laparoscopic or natural orifice surgery with a system comprising (i) an anchor or suspension element that is attachable or mountable to or mountable adjacent to an interior wall of a body cavity; (ii) at least one guide element attached to the anchor or suspension element, wherein the at least one guide element allows for dynamic manipulation of at least one structure in at least one direction; and (iii) the at least one structure attached to a suture that is positionable in the at least one direction by the at least one guide element; wherein the system is capable of being at least partially delivered into the body cavity through a single port to manipulate tissue intracorporeally while being controlled extracorporeally, the method comprising:
   a) making a single incision in a wall of the body cavity to create an opening through which the system is passed;
   b) passing the anchor or suspension element through an interior diameter of the single port port and attaching the anchor or suspension element to or mounting the anchor or suspension element adjacent to the interior wall of the body cavity;
   c) passing the at least one structure attached to the at least one suture through the at least one guide element attached to the anchor or suspension element; and
   d) controlling the at least one structure intracorporeally by dynamically manipulating the suture extracorporeally, whereby the at least one structure moves in the at least one direction intracorporeally within the body cavity;
   wherein the at least one guide element defines at least one of a loop, a notch, a grid or a hook through which the suture passes;
   wherein the suture defines three segments including (i) a first segment extending from an extracorporeal position of the single port, through the interior diameter of the single port and to an intracorporeal position of the single port inside the body cavity, (ii) a second segment extending from the intracorporeal position of the single port to the anchor or suspension element, and (iii) a third segment extending from the anchor or suspension element to the tissue,
   wherein the second segment defines a lateral spacing between the intracorporeal position of the single port and the anchor or suspension element; and
   wherein the anchor or suspension element and the at least one guide element provide leverage for moving the at least one structure intracorporeally within the body cavity.

20. The method according to claim 19, comprising insufflating the body cavity to a suitable pressure prior to step b).

21. The system according to claim 1, wherein the anchor or suspension means is attached or mounted adjacent to the tissue intracorporeally by stitching or hooking the anchor or suspension means into the tissue intracorporeally.

22. A system for performing a single-port laparoscopic or natural orifice surgery that can be at least partially delivered into a body cavity to manipulate tissue intracorporeally while being controlled extracorporeally, said system being capable of being passed through an interior diameter of a port into the body cavity, the system comprising:
   a) an anchor or suspension element, wherein the anchor or suspension element is attached or mounted adjacent to the tissue intracorporeally;
   b) a guide element attached to the anchor or suspension element, wherein the guide element allows for dynamic manipulation of at least one structure in at least one direction; and
   c) the at least one structure attached to a suture that is passable through the interior diameter of the port and positionable by the guide element;
   wherein the anchor or suspension element and the guide element provide leverage for moving the at least one structure intracorporeally;
   wherein the guide element defines at least one of a loop, a notch, a grid or a hook through which the suture passes;
   wherein the suture defines three segments including (i) a first segment extending from an extracorporeal position of the port, through the interior diameter of the port and to an intracorporeal position of the port inside the body cavity, (ii) a second segment extending from the intracorporeal position of the port to the anchor or suspension element, and (iii) a third segment extending from the anchor or suspension element to the tissue,
   wherein the second segment defines a lateral spacing between the intracorporeal position of the port and the anchor or suspension element; and
   wherein the at least one structure is controllable relative to the tissue extracorporeally by dynamically manipulating the suture extending from the interior diameter of the port extracorporeally, whereby the at least one structure moves in the at least one direction intracorporeally.

23. A system at least partially deliverable into a body cavity via a port or natural orifice during a laparoscopic or natural orifice procedure to dynamically manipulate tissue intracorporeally via dynamic extracorporeal control, the system comprising:
   a) an anchor passable through the port or natural orifice and attachable to a first intracorporeal tissue not to be manipulated, the anchor being laterally spaced from the port or natural orifice;
   b) a guide element integral with the anchor;
   c) a suture disposed in contact with the guide element and through the port or natural orifice, the suture defining a first extracorporeal end portion and a second intracorporeal end portion, the suture being dynamically movable with respect to the guide element; and
   d) at least one tissue engaging structure attached to the second intracorporeal end portion of the suture and attachable to a second intracorporeal tissue to be dynamically manipulated,
   wherein the guide element defines at least one of a loop, a notch, a grid or a hook through which the suture passes;
   wherein a lateral spacing between the anchor and the port or natural orifice forms an angled pulley with the at least one tissue engaging structure, and
   wherein pulling the suture extracorporeally away from the port or natural orifice causes the second intracorporeal tissue secured to the at least one tissue engaging structure to be lifted towards the guide element.

24. The system according to claim 23, wherein pulling the suture extracorporeally away from the port or natural orifice with a greater force causes the second intracorporeal tissue secured to the at least one tissue engaging structure to be lifted closer towards the guide element.

* * * * *

UNITED STATES PATENT AND TRADEMARK OFFICE
CERTIFICATE OF CORRECTION

PATENT NO. : 8,827,891 B2
APPLICATION NO. : 12/733095
DATED : September 9, 2014
INVENTOR(S) : Kurt Eric Roberts It is certified that error appears in the above-identified patent and that said Letters Patent is hereby corrected as shown below:

In the specification:

Column 1
Insert at line 15 -- STATEMENT REGARDING FEDERALLY SPONSORED RESEARCH
      This invention was made with government support under Grant No. RR024139 awarded by National Institutes of Health (NIH). The government has certain rights in the invention. --

Signed and Sealed this
Twenty-fifth Day of November, 2014

Michelle K. Lee
*Deputy Director of the United States Patent and Trademark Office*